(12) United States Patent
Kendall et al.

(10) Patent No.: US 8,379,993 B2
(45) Date of Patent: Feb. 19, 2013

(54) IMAGE ANALYSIS

(75) Inventors: Edward J. Kendall, St. John's (CA); Michael Gordon Barnett, Prince Albert (CA)

(73) Assignees: Edward Joseph Kendall, St. John's (CA); Michael Gordon Barnett, Prince Albert (CA)

( * ) Notice: Subject to any disclaimer, the term of this patent is extended or adjusted under 35 U.S.C. 154(b) by 353 days.

(21) Appl. No.: 12/808,099

(22) PCT Filed: Dec. 12, 2008

(86) PCT No.: PCT/CA2008/002132
§ 371 (c)(1),
(2), (4) Date: Aug. 24, 2010

(87) PCT Pub. No.: WO2009/073963
PCT Pub. Date: Jun. 18, 2009

(65) Prior Publication Data
US 2010/0310183 A1    Dec. 9, 2010

Related U.S. Application Data

(60) Provisional application No. 61/013,379, filed on Dec. 13, 2007.

(51) Int. Cl.
*G06K 9/62* (2006.01)
(52) U.S. Cl. ........................ 382/224; 382/228
(58) Field of Classification Search .......... None
See application file for complete search history.

(56) References Cited

U.S. PATENT DOCUMENTS

| | | | |
|---|---|---|---|
| 5,598,481 A * | 1/1997 | Nishikawa et al. | 382/130 |
| 5,825,936 A * | 10/1998 | Clarke et al. | 382/261 |
| 6,198,838 B1 | 3/2001 | Roehrig et al. | |
| 6,310,967 B1 * | 10/2001 | Heine et al. | 382/128 |
| 6,434,261 B1 | 8/2002 | Zhang et al. | |
| 6,650,766 B1 | 11/2003 | Rogers | |
| 6,941,323 B1 | 9/2005 | Galperin et al. | |
| 6,996,549 B2 | 2/2006 | Zhang et al. | |
| 7,054,473 B1 | 5/2006 | Roehrig et al. | |
| 7,181,056 B2 * | 2/2007 | Campanini et al. | 382/132 |
| 2005/0169529 A1 * | 8/2005 | Owechko et al. | 382/190 |

FOREIGN PATENT DOCUMENTS

| | | |
|---|---|---|
| WO | 2006114003 | 2/2006 |
| WO | 2007090892 | 8/2007 |

OTHER PUBLICATIONS

Sarty, et al., "Self-Diffusion Maps from Wavelet De-Noised NMR Images", Journal of Magnetic Resonance, Series B III, 1996, pp. 50-60.

(Continued)

*Primary Examiner* — Li Liu
(74) *Attorney, Agent, or Firm* — Anthony R. Lambert

(57) ABSTRACT

A method and apparatus for classifying an image is proposed. The image is first preprocessed by for example adjusting its orientation, selecting an area of interest and removing artifacts, and normalizing the brightness. Subsequently the image is processed by applying a wavelet decomposition and values for a scalar feature of the wavelet decomposition are measured. This value is binned and probabilities for different classifications of the image are determined based on the number of images from a training set that fall into the same bin that have each classification. Improved classifiers are constructed by aggregating the results for different features, and a network of improved classifiers, in which images are processed by later classifiers according to the results from earlier classifiers, is used.

52 Claims, 9 Drawing Sheets

OTHER PUBLICATIONS

T. Lambrou, A. Linney, and A. todd-Pokropek, in "Wavelet-based analysis and classification of liver CT", 3rd European Medical & Biological Engineering Conference EMBEC'05, Prague, Czech Republic, Nov. 20-25, 2005.

Lambrou T, Linney A, Speller R and Todd-Pokropek A. (2002). "Statistical Classification of Digital Mammograms Using Features from the Spatial and Wavelet Domains", 2nd European Conference on Medical and Biomedical Engineering EMBC, Vienna, Austria, Univ. of Portsmouth.

Cui, et al., "Automated Search for Arthritic Patterns in Infrared Spectra of Synovial Fluid Using Adaptive Wavelets and Fuzzy C-Means Analysis", IEEE Trans Biomed Eng. May 2006; 53(5): pp. 800-809.

* cited by examiner

IMAGE ANALYSIS

CROSS-REFERENCE TO RELATED APPLICATIONS

This application is a national stage entry of international application no. PCT/CA2008/002132 filed Dec. 12, 2008, and claims the benefit under 35 USC 119(e) of United States provisional application Ser. No. 61/013,379 filed Dec. 13, 2007.

TECHNICAL FIELD

Image analysis and in particular analysis of mammograms.

BACKGROUND

Breast cancer is the most commonly diagnosed form of cancer in women and the second-leading cause of cancer-related death behind lung cancer. In Canada in 2004, there were 21200 newly diagnosed cases of breast cancer and 5200 deaths from breast cancer. In the same year, there were 9800 cases of lung cancer and 8200 deaths from lung cancer.

Breast cancer increases in prevalence with age: among newly diagnosed patients, 21% are younger than 50, 49% are between 50 and 69, and 30% are 70 or older. Because of the increased risk of developing breast cancer with age, Health Canada has recommended that women over 50 receive a screening mammogram every two years; other western countries have similar screening policies in place. X-ray mammography is the primary method for early detection of breast cancer and is capable of detecting signs of cancer too subtle or small to be detected by either self-examination or routine physical examination by a physician.

X-ray mammography consists of an x-ray of the breast tissue under transverse compression. Suspicious abnormalities include clusters of microcalcifications, masses or deformations. Microcalcifications are clusters of calcium compound deposits left by several biological processes; most notably for cancer screening, they are sometimes, though not always, secreted by rapidly dividing cells such as cancer cells. Microcalcifications alone show a high correlation with breast cancer, but their appearance alone does not guarantee the presence of cancer, nor does their absence negate the possibility of cancer. Because of this uncertainty, any current automated methods which use only the presence of microcalcifications to mark suspicious images are necessarily limited in their capacity to correctly identify all images showing abnormalities.

Interpretation of mammograms is a difficult process for several reasons. Because the images are formed from x-rays passing through the tissue, contrast in the image depends on differences in the absorption rates of different materials within the tissue; however, these differences are much more subtle between the types of soft tissues in the breast than they are between bone and soft tissue in a chest x-ray, for example. The indications of cancer in an image are often also very subtle, such as small distortions in the structure of the ductile tissue of the breast or the presence of small clusters of microcalcifications.

FIG. 1 shows two typical mammography images: the left image shows a healthy patient, while the right image shows a cancerous mass. These images are medial-lateral images as signified by the ML marker on the x-ray film (the ML is reversed since the image is reflected), and are taken with the x-rays passing horizontally through the tissue while the breast is compressed between two vertical plates. The other common image view is cranial-caudal, typically denoted as CC, which is taken with x-rays passing vertically through the tissue while the breast is compressed between two horizontal plates. Breast tissue can vary greatly in appearance between patients depending on the relative amounts of glandular and fatty tissue present, which appear as relatively bright and dim regions, respectively, further adding to the challenge of detecting abnormalities within a particular patient's image.

A major challenge in the interpretation of mammograms is the small percentage of images that show abnormalities. One typical clinic diagnosed 6.4 cancers per 1000 patients; at two medial-lateral images per patient, this means only one in 300 images showed signs of cancer. This low rate of incidence potentially decreases specificity; a larger number of normal images that are classified as abnormal. Since positive findings require a patient to undergo further procedures this adds cost to the system and creates potentially unfounded anxiety in the patient. For example, in the above study 5-7% of women were recalled for further tests, though only one in ten of those recalled were actually positive for cancer.

Typical computer aided detection (CAD) systems deal with the subtlety of cancer signs on images by marking all suspicious regions in images for radiologists to re-examine. This approach may increase the number of cancer cases which are correctly diagnosed, but it also increases the number of images that a radiologist must study in greater detail and may increase the number of healthy patients recalled as being suspect for cancer. The performance of these systems is no better than that of a general radiologist reading a film.

SUMMARY

In an approach for CAD design, a method and related apparatus for analysis of an image does not attempt to localize the pathology. Instead, it pre-screens the images and removes those which are least likely to contain abnormalities. Since a greater fraction of the remaining images will contain pathology this approach reduces inconsequential reading volume and potentially reduces the number of errors generated.

There is proposed an image analyzer which in one embodiment comprises a first stage configured to accept as input a digital image comprising pixel values and render the digital image comparable to properties of a training set of images; a second stage having as input the rendered digital image, the second stage being configured to apply to the rendered digital image at least one calculation to all pixel values in the rendered digital image to generate at least one single value representative of the digital image; and a classifier configured to operate on the at least one single value and comparable single values from the training set of images and produce a classification decision.

There is also proposed an apparatus for determining a propensity for an image to fall into one of plural categories, in which in one embodiment the apparatus comprises a processing system for applying a wavelet decomposition to the image to plural levels of decomposition; a feature extractor for calculating a value for a property of the wavelet decomposition of the image at a level of decomposition; and a classifier for determining a propensity for the image to fall into one of plural categories based on the value of the property of the wavelet decomposition of the image at the level of decomposition.

A method of classifying an image is also proposed. The image is first preprocessed by for example adjusting its orientation, selecting an area of interest and removing artifacts, and normalizing the brightness. Subsequently the image is processed by applying a wavelet decomposition and values for a scalar feature of the wavelet decomposition are measured. This value is binned and probabilities for different classifications of the image are determined based on the number of images from a training set that fall into the same bin that have each classification. Improved classifiers are constructed by aggregating the results for different features, and a network of improved classifiers, in which images are processed by later classifiers according to the results from earlier classifiers, is used in the preferred embodiment.

A method of image analysis is also proposed that determines the propensity for an image to fall into one of plural categories. In an embodiment of this method, method steps comprise applying a wavelet decomposition to the image to plural levels of decomposition; calculating a value for a property of the wavelet decomposition of the image at a level of decomposition; and determining a propensity for the image to fall into one of plural categories based on the value of the property of the wavelet decomposition of the image at the level of decomposition.

A method of reducing workload of a physician is also proposed, which in one embodiment comprises obtaining a digital image of human tissue, the digital image comprising pixel values; in at least a pre-classification step, processing the digital image to render the digital image comparable to properties of a training set of images; applying at least one calculation to all pixel values in the digital image to generate at least one single value representative of the image; classifying the digital image as normal or not-normal by comparing the at least one single value to comparable single values from the training set of images; and having the physician review the digital image only if the digital image is not-normal.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

A tool is proposed that accurately determines if a mammogram contains abnormalities. Exemplary embodiments of the tool's design are discussed below, and discussed in relation to a specific practical example, referred to as the example given here, wherein a known set of images are analyzed.

In an embodiment, digitized images are first processed to make the images comparable to a training set of images (which may also be processed for this purpose), as for example to remove artifacts and reduce noise. Depending on the images, little or no processing need be carried out. Next, pixel values in the digital image are subject to at least one calculation to generate at least one single value representative of the image, as for example by decomposition into a set of wavelet maps from which scalar features are generated. The digital image may then be classified as normal or not-normal by comparing the single value to comparable single values from the training set of images, as for example using a modified naïve Bayesian classifier in a "concerted effort" configuration. A physician need only review the digital image if the digital image is classified as not-normal.

1. Complete Image Analysis System

Figure 1:
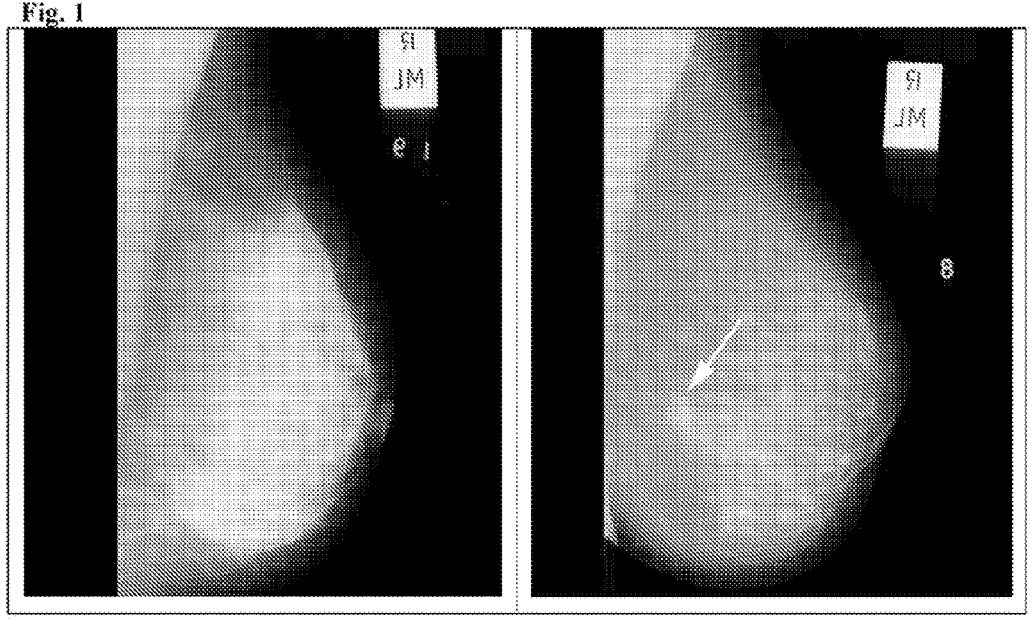
FIG. 1 is a pair of typical mammograms showing healthy tissue (left) and showing a cancerous mass (right, marked with white arrow)
Figure 2:
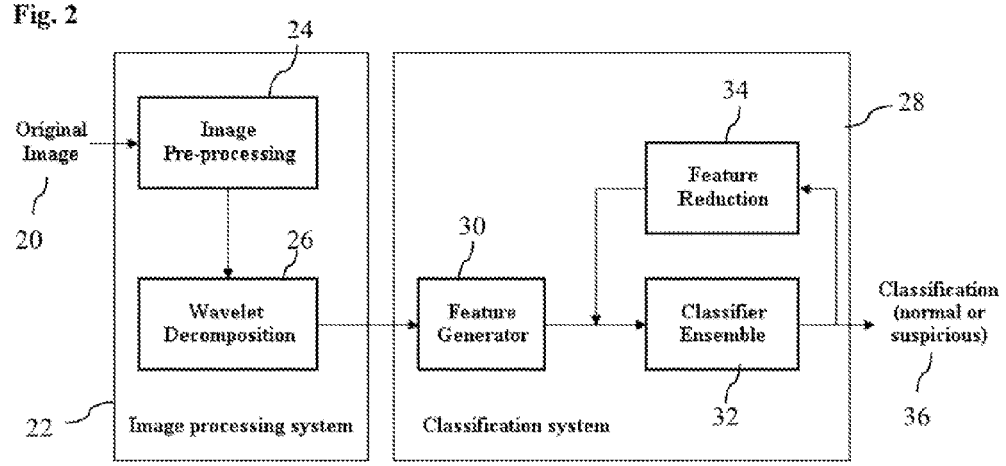
FIG. 2 is a block diagram of an exemplary image classification system.

An example of an entire image analysis system, from the reading of the original image 20 to the final classification 36 as either normal or suspicious, is represented by the block diagram as shown in FIG. 2. The system of this example comprises two distinct stages: the image processing system 22, which reads in the original image and produces a set of wavelet map images for the classifier to use; and the classification system 28, which measures features from the wavelet images and classifies the image as either normal or suspicious based on the results from the ensemble of classifiers.

The image processing system comprises two discrete stages: the image pre-processor 24 and the wavelet decomposition system 26. In some embodiments, the calculations could be combined into a single mapping but the mapping in such embodiment would still effectively be decomposable into two distinct stages and therefore be effectively the same thing as two stages. The image pre-processor takes the original digitized mammography image as an input and outputs a normalized image. The normalized images are oriented, intensity scaled, have background artifacts 40 (FIG. 3) removed and are background thresholded to zero to remove noise. The wavelet decomposition system accepts these normalized images and carries out a wavelet analysis on them using one of a number of possible wavelet bases. Multiple levels of decomposition are used, and four images are produced at each level of the decomposition, so that the output of the wavelet decomposition system is a set of images forming the wavelet maps of the normalized version of the original input image. The classification system comprises three stages: the feature generator 30, the classifier ensemble 32, and the feature reduction system 34. The feature generator reads in the set of wavelet maps produced by the image processing system and reduces them to a set of scalar features. Section 3 discusses the generation of features from the wavelet maps. The classifier ensemble may comprise a set of naïve Bayesian classifiers working in tandem to produce a single classification output of normal or suspicious using the features from the feature generator as input. Feature reduction is used to minimize the number of features used to make the classification.

2. Image Pre-processing

The sample images analyzed in the example given here were taken from the Mammographic Images Analysis Society's digital mammogram database that consisted of 284 images: 204 images of normal breasts and 79 images showing one of four pathologies: benign masses, cancerous masses, benign calcifications or cancerous calcifications. There were an approximately equal number of images of right and left breast images; all were medial-lateral images. In general, the classifier may be applied to any digital mammogram.

To reduce the influence of information content not related to pathology, several pre-processing steps may be implemented to regularize the appearance of the images and remove any unnecessary artefacts: orientation matching, background thresholding, artefact removal and intensity matching.

2.1 Orientation Matching

Figure 11:
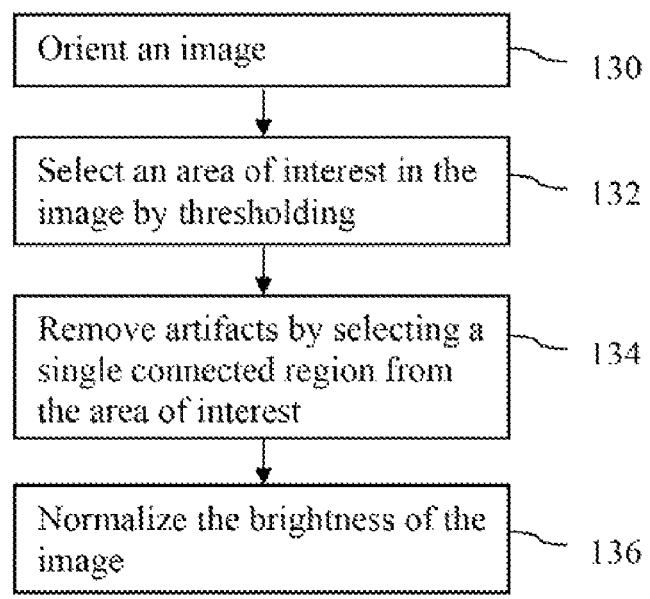
FIG. 11 shows a pre-processing method.

Because the images of right and left breasts point to the left and right sides of the image, respectively, the images of right breasts may first be flipped horizontally to have the same orientation. A major feature in all images that this affects is the sharp vertical line between the tissue and the dark background where the original film ends: on left breast images the intensity rises left to right across this edge, while on right breast images it falls, changing the sign of the calculated wavelet coefficient; matching the orientations of all images prevents this artefact from appearing in later analysis (step 130, FIG. 11). In some cases, such as where only left images are imaged or if the imaging technology already re-orients the mages, this step may be omitted.

2.2 Background Thresholding

Since the pathology information is contained entirely within the tissue region of the image, no signal should be present in the dark background. Thresholding is a technique which sets all pixels below a set intensity level to zero; to accomplish this, a conservative threshold value may be chosen to be half of the threshold predicted by Otsu's Method. In Otsu's method, a threshold level is chosen such that all background pixels have an intensity below the threshold value and all foreground object pixels have intensity above the threshold value. In practice, the intensities of foreground and background pixels have broad, overlapping distributions, and it will not be possible to choose a threshold value which does not misclassify any pixels. Otsu's method chooses a threshold level which minimizes the segmentation error between the two regions. In the results described here, the actual threshold level used was half of that predicted by Otsu's method; this is done to reduce the number of pixels from the tissue which are misclassified as background pixels and thus removed from the image. It is believed that this step did not significantly reduce the sensitivity of the classification. Since the intensity in the images is directly related to the attenuation of x-rays passing through the tissue, and since this attenuation depends largely on the thickness and density of the tissue, tissue pixels which fall below the conservative threshold are predominantly from the edges of the tissue region where the breast tissue is thin and uncompressed. Any pathology that exists this close to the surface of a patient's skin should be readily detectable by conventional examination without the aid of mammography. In some embodiments, such as for example where a dark background is not present, this step may be omitted and in addition other steps may be used to remove the background, the example given being exemplary. Other methods may also be used to identify areas of interest and set pixel values in other areas of interest to zero, such as by edge detection. See step 132, FIG. 11).

The thresholding process 132 may be implemented in conjunction with the next step, artefact removal; because of this, it may be convenient to perform a binary thresholding, where all pixels below the threshold are set to an intensity of zero and all pixels above the threshold are set to an intensity of one. The resulting image may be used as a mask for the original image: the output image of the process is the pixel-by-pixel product of the binary image with the original, so that all background pixels are set to an intensity of zero and all foreground pixels were unaffected.

2.3 Artefact Removal

Figure 3:
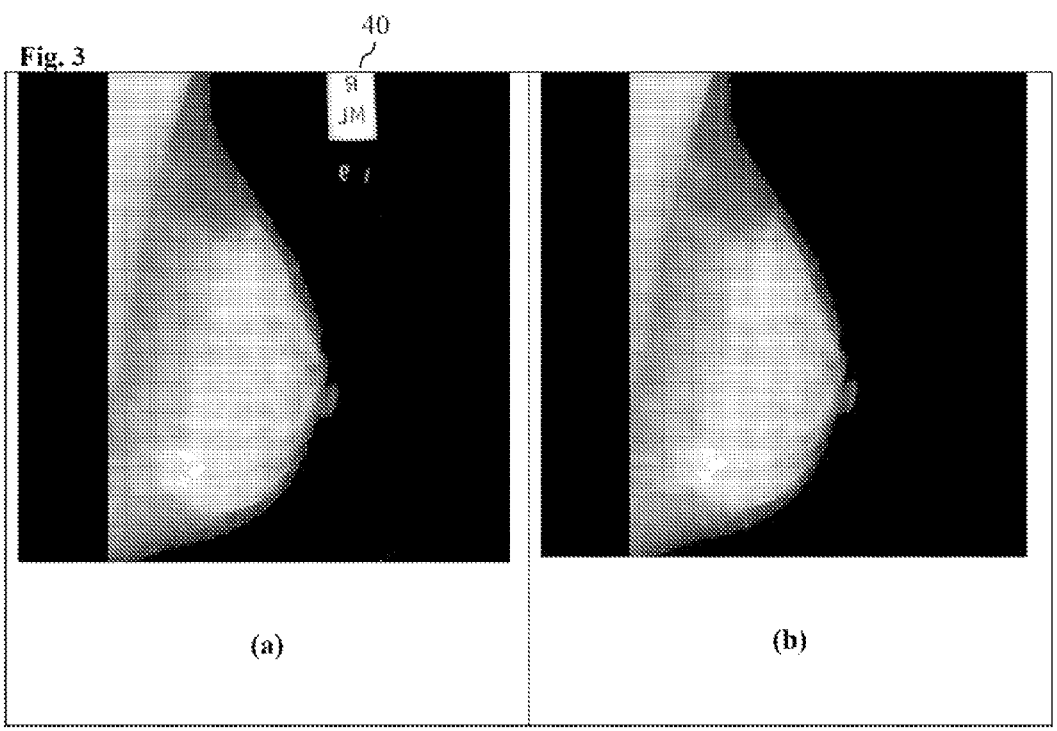
FIG. 3 is a mammography image before (a) and after (b) an artefact removal procedure.

Once the binary image is created through thresholding, it is possible to remove artefacts in the image (step 134). The image is labelled as a set of contiguous regions, typically 100-125, consisting of 4-connected groups of white pixels in the binary image. Two pixels are part of a 4-connected region if it is possible to travel between them by moving only vertically or horizontally (not diagonally) from pixel to pixel, travelling only on pixels that are part of the 4-connected region. To preserve the tissue, in the specific example shown, all labelled regions are removed from the image except for the one containing the centre pixel in the image: since the breast tissue is centred in all images, this approach isolates the breast tissue in all 284 images used. The most noticeable artefact 40 removed is the "ML" view tag, although a large number of small regions in the background which were brighter than the threshold level in the previous step are removed by this procedure. FIG. 3 shows an image before and after the artefact removal step has been applied.

2.4 Intensity Normalization

The final pre-processing step that may be applied to the images before they are ready for wavelet decomposition is the intensity normalization step 136. This step scales all images so that the intensity of the brightest pixel in the image has a relative intensity of 1.0 and linearly scales all other image pixels accordingly. The transformation is described by:

$$\text{img\_out} = \frac{\text{img\_in}}{\max(\text{img\_in})},$$

where img_in is the input image following the artefact removal step and img_out is the intensity matched image whose pixel intensities range from zero to one. This step ensures uniformity across different images, which may be taken at different times under slightly different machine settings or by different personnel. Other methods may be used to normalize the images, and some embodiments, normalization may not be necessary.

2.5 Wavelet Decomposition of Processed Images

Figure 9:
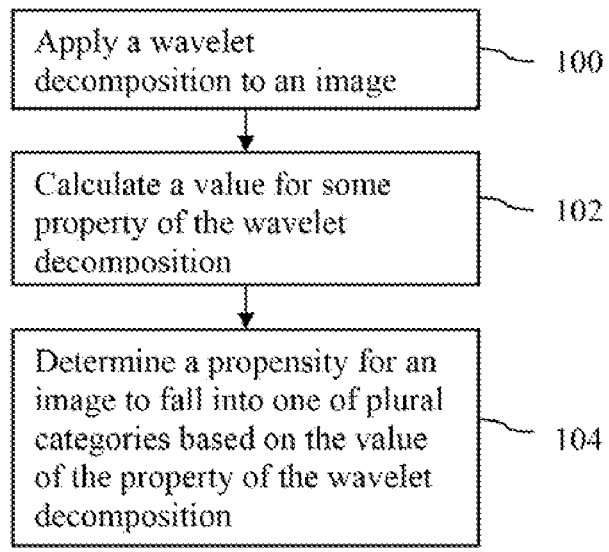
FIG. 9 shows a method for classifying an image.
Figure 10:
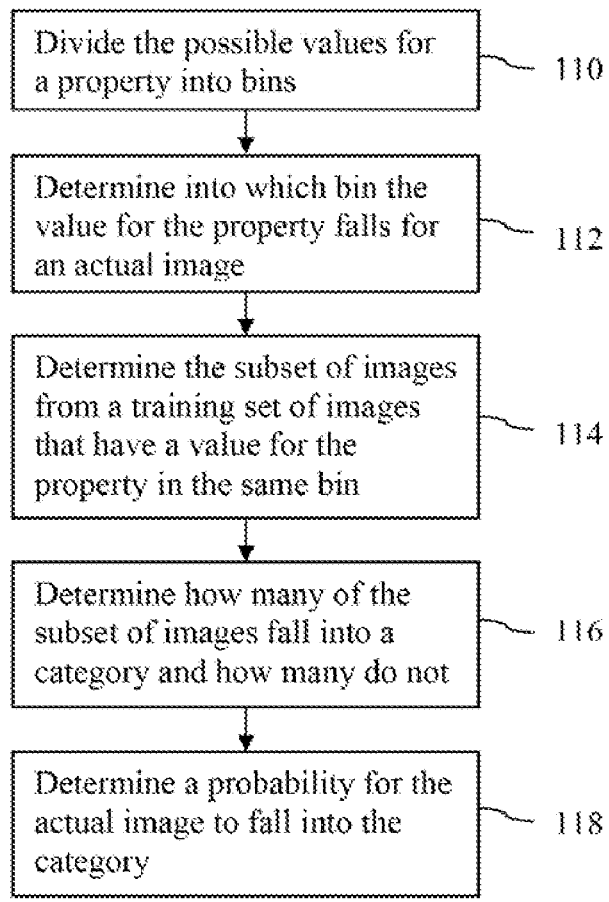
FIG. 10 shows a method for classifying an image based on binning.

Once the images are pre-processed to minimize the differences between images that are not related to differences in the physical composition of the breast tissue, a calculation such as wavelet analysis may be performed on the images (step 100, FIG. 9). The discrete two-dimensional wavelet transform is applied directly to the images. The images may, as used in the specific example given, be all sampled to 1024× 1024 pixels, which allows 9 levels of decomposition, since dyadic sampling reduces the dimensions by a factor of two in each direction after each pass. In the example given, only eight levels of decomposition were used.

2.5.1 Choice of Wavelet Basis

Figure 4:
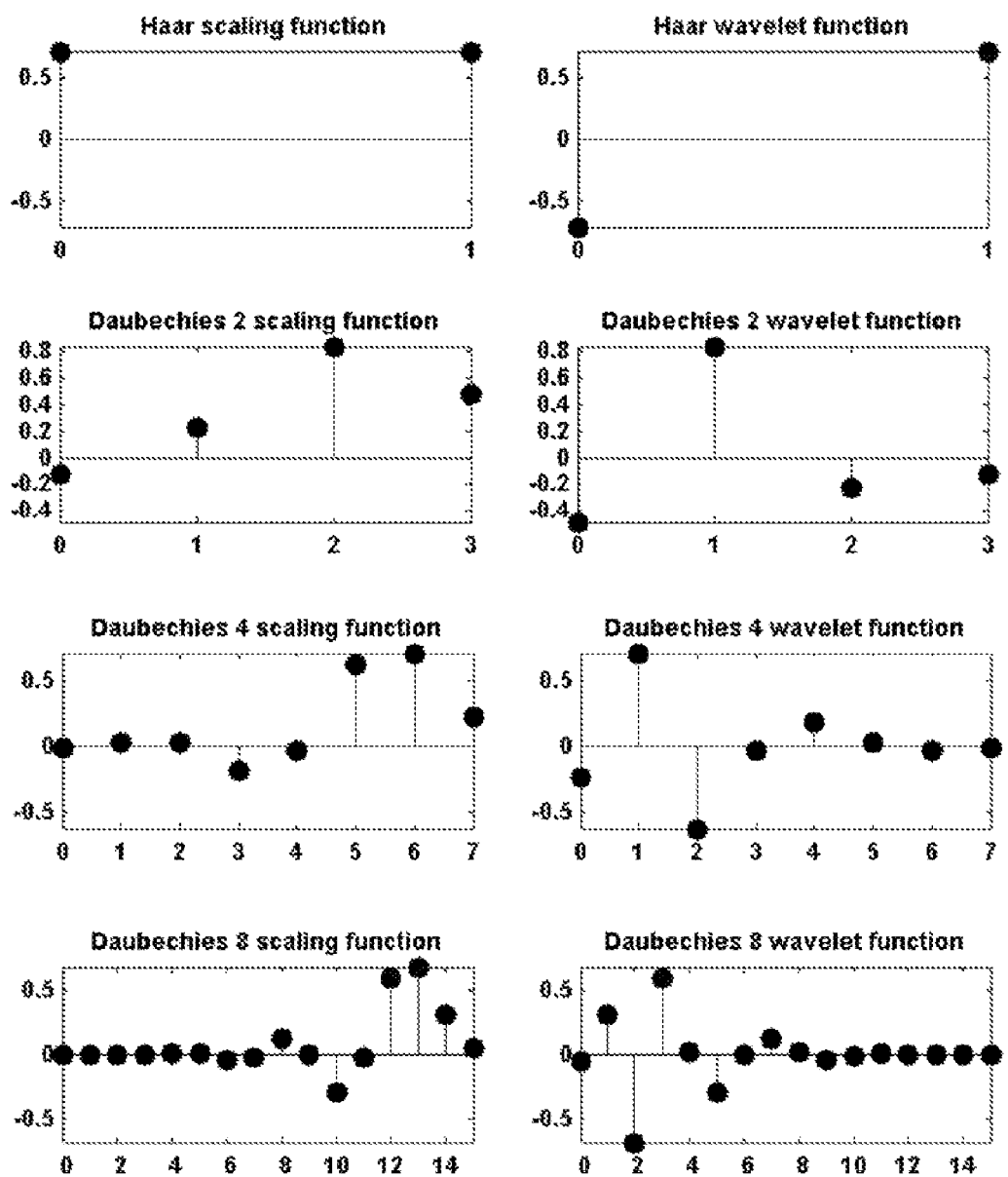
FIG. 4 shows the wavelet functions (high pass filters) and scaling functions (low pass filters) for exemplary Haar and Daubechies wavelet bases used.
Figure 5:
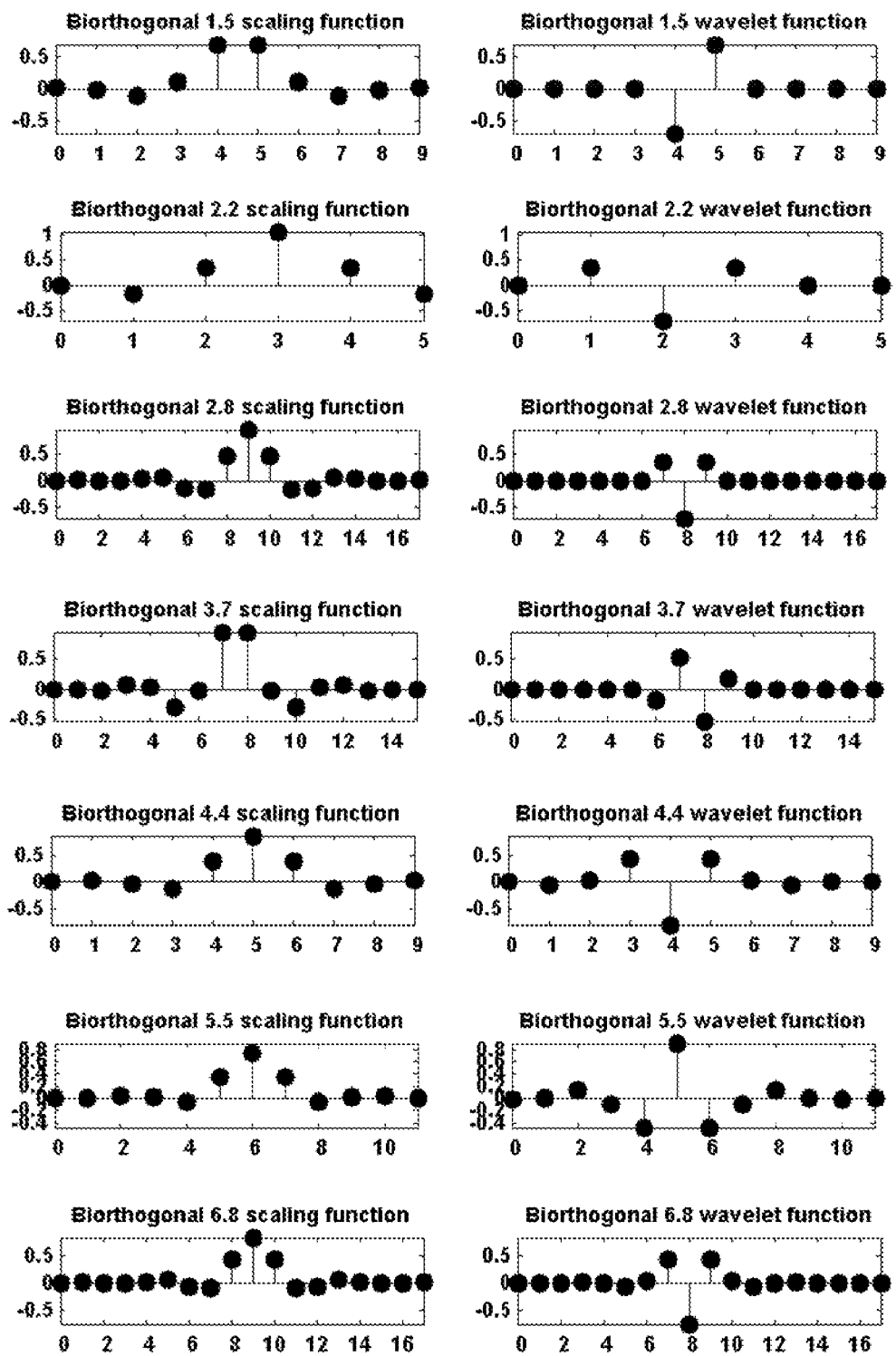
FIG. 5 shows the wavelet functions (high pass filters) and scaling functions (low pass filters) for exemplary Biorthogonal wavelet bases used.

A large number of wavelet bases have been developed in the literature, and new wavelet bases may be constructed easily, making the selection of an optimal basis for a particular task a complex project on its own. Here, a representative sample of widely used wavelets was used. Though this approach was unlikely to find the optimal wavelet basis for this type of signal processing, it is believed that the use of any sufficiently carefully chosen wavelet base can produce strong results, and the difference between optimal and sub-optimal wavelet bases is typically small. Eleven wavelet bases were tested in this work and are given as examples: the Haar wavelet; the Daubechies 2, 4 and 8 wavelets; and the biorthogonal 1.5, 2.2, 2.8, 3.7, 4.4, 5.5 and 6.8 wavelets. The Haar wavelet was chosen for its simplicity and for its effectiveness at detecting sharp contrasts, such as we anticipated for microcalcifications against a relatively dark background. The Daubechies wavelets were chosen for their sensitivity to various types of intensity gradients. The biorthogonal wavelets were chosen for their ability to provide exact reconstruction. FIG. 4 shows the Haar wavelet and the 3 Daubechies wavelets used in this work, and FIG. 5 shows the 7 Biorthogonal wavelets used in this work. The wavelets and their associated scaling functions are shown in their discrete form, since this was the form used to decompose the mammographic images. Note that the wavelet functions correspond to the high pass filters and the scaling functions correspond to the low pass filters applied along either the horizontal or the vertical directions in an image.

Figure 6:
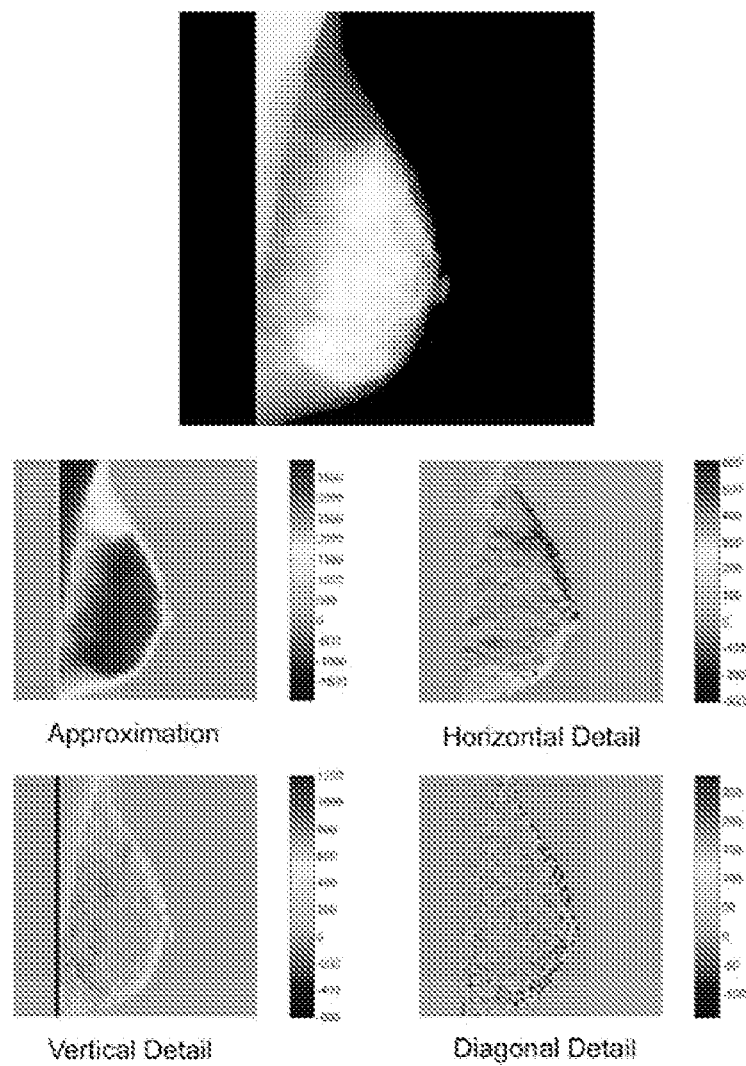
FIG. 6 is an original mammography image (top) and 4 output views at the third level of decomposition using a Haar wavelet basis.

FIG. 6 shows the four views obtained at the third decomposition level when the Haar wavelet basis is used. Resolution at this scale is 128×128 pixels. Note that the wavelet maps have a lower resolution than the original image, and that each view is sensitive to different features in the image: the horizontal detail detects vertical changes in intensity, the vertical detail detects horizontal changes in intensity, the diagonal detail responds when the intensity is varying in both directions, and the approximation image is a low resolution version of the input image used and that is used in turn as an input to the next coarser level of the decomposition.

The use of the wavelet transform offers several advantages over other transforms, such as the Fourier transform, that may be used to parse the mammography images. The primary advantage is the property of multiresolution: the wavelet maps at different levels emphasize to different sized features. Masses may range in diameter from a few millimeters to a few centimeters. Nevertheless, the multiresolution feature of wavelets permits the same algorithm to be used to sensitively scan for their presence. Microcalcifications tend to be quite small and are fairly similar in size, so multiresolution is less useful for detecting these abnormalities.

The second advantage of the wavelet transform is its retention of spatial location information. The produced maps show the spatial distribution of information at particular size scales; in contrast, the Fourier transform would lose the spatial information and simply produce a map of the relative contributions of different frequencies over the entire image. This spatial dependence is useful for finding localized structures, such as microcalcifications and small masses, which remain localized after the wavelet transform has been applied and can then be distinguished from a more homogeneous background.

2.6 Generation of Scalar Features

Once the wavelet maps have been generated from the pre-processed images, scalar features are extracted to be used in the classification process (step 102, FIG. 9). All features extracted in the example given were whole-image statistical features, and the resulting classification scheme classified whole images as being normal or suspicious, rather than locating suspicious regions within an image. In the example given, four features corresponding to properties of the decomposed image are extracted from each wavelet map: the mean intensity, the standard deviation of the pixel intensities, the skewness of the pixel intensities and the kurtosis of the pixel intensities, although other properties may be used in some embodiments. Several corrections were applied to the wavelet maps before calculating these features to emphasize the effects of abnormalities on their values; these corrections are discussed in Section 2.6.1. Following that, Sections 2.6.2 to 2.6.5 discuss how each statistic is calculated and their physical interpretation, which governs their utility in distinguishing between normal and suspicious images.

2.6.1 Corrections for Breast Size and Directionality of Wavelets

To make the scalar features extracted from the wavelet maps as physically meaningful as possible, several corrections may be applied to the raw statistical measures taken from the images. Specifically, the absolute values of the pixels in the wavelet maps may be used rather than their signed values to focus only on the strength of the correlation between the wavelet basis function and the underlying image at the current scale. Secondly, a correction may be made for the size of the breast tissue region within the image to keep it from skewing the feature values, which should ideally only vary between images because of differences in pathology and structure in the tissue.

A wavelet map contains both positive and negative values, corresponding to positive and negative correlations between the wavelet and the image. For example, the Haar wavelet transform produces positive values for a rising edge and negative values for a falling edge as it moves left to right across an image. However, the directionality of the structures in the images, such as microcalcifications, is not as important as their presence or absence, and so only the magnitudes of the wavelet maps were used. As well, the mixture of positive and negative values can partly compensate for each other in the calculation of mean intensity and other features; this reduces the difference between the values measured from different images, making it more difficult to classify images based on this feature. To reduce the effect of breast size alone on the resulting scalar features, all statistical values may be measured only for pixels within the region corresponding to the actual breast tissue. This may be done by using the approximation image at each level as a mask: a given pixel in an image is only used in a calculation if the corresponding pixel in the approximation image at the same level is non-zero, meaning that it corresponded to tissue. Without this correction, the statistical features may be skewed to higher values for larger breasts, obscuring the more meaningful differences in values caused by the presence or absence of abnormalities. For example, the measured mean intensity of an image would be twice as large for tissue that covered twice as much of the image even if the mean intensities within the tissue regions themselves were the same. The corrections may be made by appropriate configuration of the image processing system or the classification system or both.

2.6.2 Mean Intensity

A first scalar feature or property value used may be the mean intensity of the wavelet map. The mean intensity u may be calculated only for pixels within the tissue area as follows:

$$\mu = \frac{1}{N} \sum_{i,j} I(i, j),$$

where N is the number of pixels in the tissue region of the image, I(i,j) is the pixel intensity of the pixel in row i, column j of the image and the summation runs over all pixels defined by the image mask.

The mean intensity feature value gives a measure of the fraction of the total information in the original image present at the current scale. The horizontal, vertical and diagonal detail images' mean intensities show the high frequency information at the current scale, while the approximation image shows the information left in all larger scales. Lower levels of the decomposition corresponding to larger scales will then parse the approximation image and show how its information is in turn distributed among all larger scales.

The presence of microcalcifications should skew the total energy of an image towards the higher resolution, lower spatial scale maps, since the deposits are small in size and bright in appearance. In tissue containing calcifications, then, the high resolution maps should have a slightly higher intensity and the low resolution maps should have a slightly lower intensity than the corresponding maps produced from a normal sample. In reality, the effect of the small microcalcifications on the total image intensity is small and easily reduced by other, normal variations between different samples; this drawback does not make this statistic invalid, but it motivates the use of multiple measures from several images in tandem to fully differentiate between normal and suspicious tissue.

The other sign of pathology is the presence of a mass in the image. A mass may have almost any size, from a few millimeters to several centimeters in width. As well, a mass may have a sharp boundary, or it may have a speculated appearance with tendrils extending into surrounding tissue, especially for the case of malignant, cancerous masses. This large variety in the appearance of masses in an image means that no single scale or wavelet basis will naturally extract all masses from the background tissue. All masses do share the property of being localized in one region of the tissue, though, and they typically appear as slightly brighter regions due to their slightly higher density as compared to healthy tissue. Hence, a particular wavelet basis may measure a slightly larger than normal mean intensity at a particular scale and view when a mass is present, and this may make it possible to identify images showing the presence of masses automatically, especially when the feature values from several different scales are used in conjunction to detect masses of differing sizes.

2.6.3 Standard Deviation of Pixel Intensities

A second scalar feature generated from the wavelet maps may be the standard deviation of the pixel intensities in the wavelet maps. The standard deviation $\sigma$ is calculated over all pixels within the tissue region as follows:

$$\sigma = \sqrt{\frac{1}{N}\sum_{i,j}[I(i,j)-\mu]^2}.$$

The standard deviation measures the variability in the brightness of the image over the tissue region. Microcalcifications much brighter than the mean image intensity will raise the standard deviation measure of the high spatial resolution levels of the wavelet map images as compared with the corresponding images from a sample with no visible microcalcifications. Masses may affect the standard deviation of the image in a similar fashion, but at lower spatial resolution scales corresponding to the approximate size of the mass.

The major drawback of using the standard deviation as a measure for detecting abnormal pathologies is the variation in tissue appearance among healthy patients. One contributor to this variation is the amount of stromal and glandular tissue present in different patients.

2.6.4 Skewness of Pixel Intensities

A third statistic measured from each wavelet map image may be the skewness of the pixel intensities. The skewness of a distribution of values is defined as the third central moment of the distribution, normalized by the cube of the standard deviation. Symbolically, the skewness S is calculated according to:

$$S = \frac{1}{MN}\sum_{i,j}\left[\frac{I(i,j)-\mu}{\sigma}\right]^3.$$

The skewness of a distribution measures the degree of asymmetry. Consider, for example, a distribution which is approximately Gaussian. If the left tail is slightly larger than the right tail, the distribution has a negative skewness; if the right tail is slightly larger, the distribution has a positive skewness. This statistic is sensitive to the addition of a small number of unusually small or large values to a distribution, which may alter the skewness even if the mean value or standard deviation is not significantly altered.

Because of its sensitivity to a small number of additional large-valued points, skewness is a good candidate for detecting the presence of microcalcifications in an image. The calcifications, which are only a few pixels in size at even the highest resolutions but are unusually bright, can skew the distribution of pixel intensities in the wavelet map of an image in a measurable way.

The skewness measurement is also sensitive to the presence of masses in an image. Dense masses appear as slightly brighter than normal regions within the tissue, raising the number of pixels with intensities larger than the mean value of the distribution. Since skewness measures the imbalance between the parts of the distribution above and below the mean, the presence of a dense mass will raise the skewness relative to a healthy image. Wavelet bases and levels that correlate particularly well with the shape of a mass will show a larger effect in their skewness measure, making this approach most useful when used in conjunction with an appropriate basis.

2.6.5 Kurtosis of Pixel Intensities

A fourth statistic computed from the wavelet maps may be the kurtosis of the pixel intensities. The kurtosis of a distribution of values is defined as the fourth central moment of the distribution, normalized by the fourth power of the standard deviation of the distribution. Symbolically, the kurtosis K is calculated according to:

$$K = \frac{1}{MN}\sum_{i,j}\left[\frac{I(i,j)-\mu}{\sigma}\right]^4.$$

Qualitatively, kurtosis measures the narrowness of the central peak of a distribution compared with the size of the distribution's tails. A distribution with a narrow peak and tails that drop off slowly has a large kurtosis compared with a distribution with a relatively wide peak but suppressed tails. Kurtosis is positive definite for a real-valued distribution of values. The kurtosis and standard deviation of a distribution may be similar, though kurtosis is more sensitive to points distant from the mean than the standard deviation is.

Because kurtosis depends on the fourth power of the distance between an outlying point and the mean, it is highly sensitive to the addition or loss of points far from the mean of the distribution. Microcalcifications may raise the kurtosis by increasing the number of unusually bright pixels in a wavelet map, especially at the higher resolution scales where the calcifications can be differentiated.

2.7 Single naïve Bayesian Classifier

Naïve Bayesian classifiers may be used in concert to form the full classification system; each individual classifier may be constructed and trained as an individual classifier before being combined into the complete system.

The construction of a single Bayesian classifier is relatively straightforward. The input feature values from the wavelet analysis are discretized into a small number of bins to create probability distributions for each feature's value. The binned probabilities are then employed to determine the probabilities that a new sample is either normal or suspicious and classification is made based on which class carried the larger probability of producing the sample (method step 104). Several techniques used to streamline the algorithm as implemented in the specific example disclosed are discussed as they occur, since high efficiency is preferred and may be needed for the feature selection step to be able to explore a sufficient number of feature subsets.

2.7.1 Discretization of Scalar Feature Values to Form Probability Distributions

Each scalar feature measured from the wavelet maps of the normalized mammographic images varies over a continuous range of possible values. Since a leave-one-out training methodology was applied in the specific example given, there were approximately 80 suspicious and 200 normal sample values available for each feature to construct a probability distribution when the MIAS image set was used.

Many approaches to binning continuous data exist, though the differences between their accuracies are relatively small. Because of this, a simple approach may be used, and in the specific example given the data was binned into a pre-selected number of bins of equal width. To be able to compare the probability that a new sample's feature value comes from the normal or the suspicious class, the normal and suspicious probability distributions for a feature needed in this example to have the same bin widths and locations. The number of bins may be estimated using Sturgis' rule, which estimates the optimal number of bins for representing a distribution given a set of sample points. Sturgis' rule estimates that the number of bins should be $1+\log_2 N$, where N is the number of points available for binning; this gives 7 bins for the suspicious distribution and 8 bins for the normal distribution. To make the two distributions comparable, a common number of bins may be chosen for both. Ultimately, 8 bins were used in the example given to discretize both distributions (step 110). The lowest bin's lower bound was set equal to the smallest sample feature value, and the highest bin's upper bound was set equal to the largest sample feature value; the remaining bin boundaries were equally spaced between these two extremes.

2.7.2 Correction for Empty Bins

A small correction factor may be applied to all bins, including the empty ones, to account for the uncertainty inherent in estimating a probability distribution from a finite sample of data points. The uncertainty in a given bin's count was in the example given taken to be the inverse of the square root of the number of data points used to estimate that distribution. In this example, the correction factor was 0.113 counts for the suspicious distribution and 0.070 counts for the normal distribution. Once the bins are filled and the correction factor applied, the bin counts may be normalized to convert the count rates into a probability density. Each bin in the example given here was normalized according to the following equation:

$$P_c(j) = \frac{1}{Wk} \frac{N_c(j)}{\sum_i N_c(i)}$$

where $P_c(j)$ is the probability of class c producing a feature value within bin j, W is the width of a single bin, k is the number of bins used, $N_c(j)$ is the number of training samples from class c falling into bin j, after the correction factor is applied, and the summation runs over all bins in the distribution (steps 112, 114, 116 and 118). In this way, the integral of the probability density over the range of possible values for a particular feature becomes equal to one.

2.7.3 Classification of Whole Image Based on Feature Probabilities

The classifier operates by determining the propensity of the image to fall into one of plural categories (step 104*m* FIG. 9). The propensity may be numerically calculated in terms of probabilities. An aggregate of propensities may be used to determine an overall propensity. For example, the discrete probability densities for each feature, once generated, may be used to classify an input image as either normal or suspicious. The probability that an image is normal or suspicious may be calculated as the product of the probabilities that each feature used from the image is normal or suspicious, although other calculations may be used to aggregate propensities. Three to five features were used at a time in the example given, but other numbers of features may be used. The ratio of the suspicious to the normal probability may be taken and used to classify the image. In the example given, if the ratio is greater than one, the image is classified as suspicious; if the ratio is less than one, the image is classified as normal.

To improve efficiency, the implementation of the probability comparison may be performed differently. For example, the ratio of the suspicious to the normal probabilities for each individual feature may be calculated first before the product over all features used is performed, rather than multiplying the different feature probabilities together first and then calculating the suspicious to normal probability ratio. Further, the logarithm of the probabilities may be used in practice, so that a product of probabilities becomes a sum of the logarithm of the probabilities, and the logarithm of the ratio of the probabilities may be used for classification instead. An image is suspicious if the logarithm of the suspicious to normal probability ratio is greater than zero or normal if it is less than zero. The use of logarithms and pre-calculated ratios eliminate the repetitive multiplication and division operations from the classification step, speeding the algorithm by an order of magnitude and allowing a larger family of possible feature subsets to be explored.

2.7 Feature Selection and Reduction

Since a large number of potential classification features are generated from each image in the embodiment disclosed here and since a classifier should use approximately one feature for every ten training samples available, a selection process may be needed to choose those features that are most effective at differentiating between normal and suspicious images. Specifically, in the example given, four parameters are measured from each wavelet map; four wavelet maps per level and eight levels of decomposition, creating 132 potential features for each of the 11 wavelet bases tried in this work. Since multiple classifiers may be used in tandem to perform the final classification, each individual classifier may be limited to use no more than three features, though one or two features may be used if it produced better results. Selecting such a small subset of the candidate features adds flexibility to the design of each individual classifier: one classifier may use a feature subset sensitive to microcalcifications while another may use a feature subset sensitive to masses.

Feature selection may be carried out through a semi-exhaustive process, if there are too many potential features to test every possible triplet's performance. Each classifier in the example given here was limited to use only one wavelet basis and two of the four types of parameters generated for the maps. The 64 features this left were then searched exhaustively: every possible triplet, doublet and singlet of features was tried on the available data, and a performance metric was developed to select the most effective combination.

The performance metric used to select the most effective feature subset in the example given was a weighted sum of the number of true positive classifications, NTP, and the number of true negative classifications, NTN. A true positive was an image with abnormalities that was correctly classified as suspicious, and a true negative was an image with no abnormalities that was correctly classified as normal. The score S produced from this was calculated according to:

$$S=w(\text{NTP})+(1-w)(\text{NTN}),$$

where w is the value of the weighting factor and varies between zero and one. A high weighting factor places more importance on correctly classifying suspicious images, a low weighting factor places more importance on correctly classifying normal images, and a weighting factor of 0.5 makes the score depend only on the number of images classified correctly, regardless of type. Another interpretation of the weighting factor is that it measures the importance of sensitivity relative to specificity; a large weighting factor favours a more sensitive classifier while a small weighting factor favours a more specific classifier.

The nature of the classification done in this work, that is, that images classified as normal are not subject to further analysis, means that any false negatives cannot be corrected for later, and therefore, the true positive fraction must be maximized. To that end, the weighting factor was chosen to be 0.995; this made the true positive fraction paramount, but in the event that two feature subsets produced the same number of true positives, the tie would be broken by selecting the feature subset which had the higher true negative fraction.

Since the individual classifiers were combined after they were tested, individual classifiers could also be designed to maximize the number of masses detected, or the number of microcalcifications detected, or any other specific type of abnormality. To search for a particular type of abnormality, NTP in equation was replaced with the number of correctly classified images with the specified abnormality, and NTN was replaced with the number of correctly classified images of all other types, including normals.

2.9 Formation of Concerted Network of Classifiers

By combining the output from several classifiers, two advantages are given: firstly, the overall accuracy of the classifier system is boosted significantly; and secondly, it becomes possible to provide confidence levels for the classifications made by the complete system.

2.9.1 Network of Classifiers Customized to Detect Particular Abnormalities

A network of individual classifiers tuned to detect particular types of abnormalities was constructed. Because of the high sensitivities of these tuned classifiers, networks constructed from them can offer extremely high classification rates.

Figure 7:
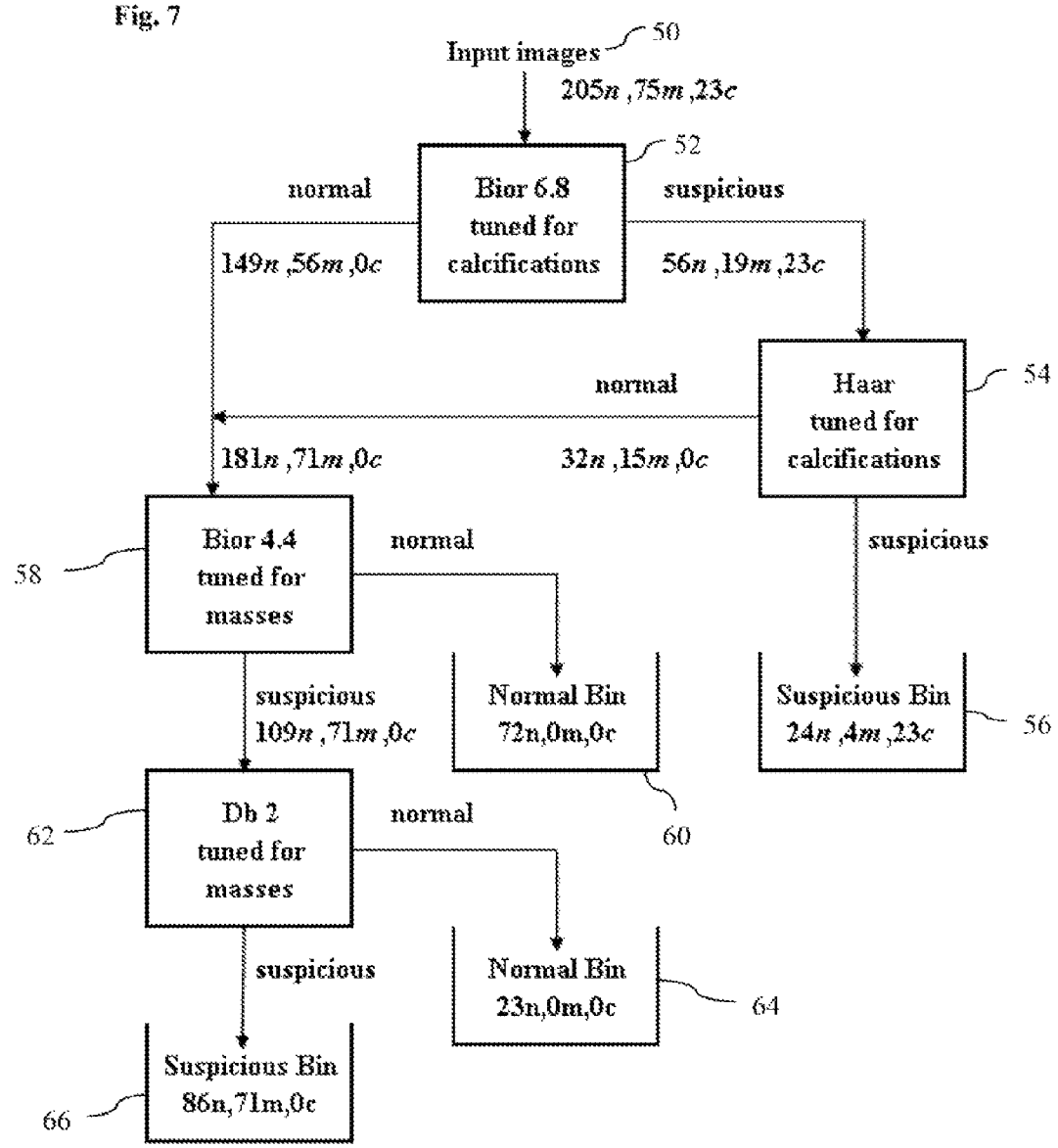
FIG. 7 shows a network for detecting abnormalities, detecting calcifications first.

The performance of the networks is shown pictorially in FIG. 7. Calcification images are filtered out first, then the other images are sorted in several passes to isolate images with masses. The individual classifiers are shown as boxes containing the type of wavelet basis and the type of abnormality the classifier is sensitive to. The two outputs from each classifier, normal or suspicious, are shown along with the number of each type of image that were classified in that way: for example, 103n, 23m, 10c means that 103 normal images, 23 mass images and 10 calcification images were given a particular classification by an individual classifier. The output bins are listed in the same way. The complete network offers 100% sensitivity and 46.4% specificity, with the high sensitivity caused by the precision of the tuned classifiers described above.

In particular, the input images 50 are first filtered by a biorthogonal 6.8 classifier 52 tuned for calcifications. Images found to be suspicious are filtered by a Haar classifier 54 tuned for calcifications; images found to be suspicious again are placed in a suspicious bin 56. Images classified as normal by either of the first two classifiers are filtered by a biorthogonal 4.4 classifier 58 tuned for masses; images found to be normal are placed in a normal bin 60, and images found to be suspicious are given to a Daubechies 2 classifier 62 tuned for masses. Finally, images found to be normal by this classifier are placed in a normal bin 64 and images found to be suspicious are placed in a suspicious bin 66.

Figure 8:
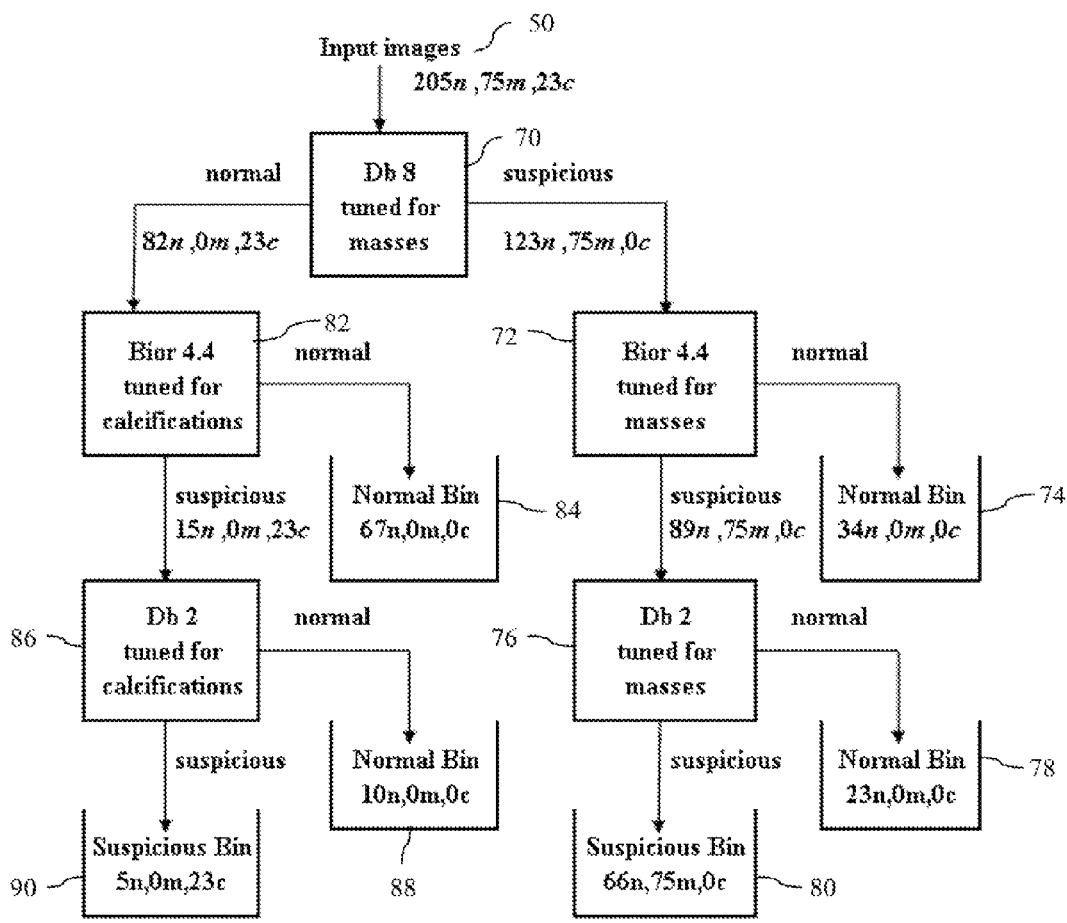
FIG. 8 shows an alternate network for detecting abnormalities, detecting masses first.

FIG. 8 shows an alternate design that first filters out the mass images, then sorts the remaining images to find the calcifications. Because the first classifier perfectly segments the calcification and mass images into two groups, two classifiers could be used on each output pool of images to achieve a high specificity. The additional classifier that is sensitive to masses is used to overcome the reduced specificity that this type of classifier has compared with classifiers that are sensitive to calcifications. The whole network had a sensitivity of 100% and a specificity of 65.4%. While more classifiers could be added to such a network, minimizing the total number of features used to classify an image makes the system more flexible and less likely to become over-specified towards the data set used for training and testing.

In particular, the input images 50 are first filtered by a Daubechies 8 classifier 70 tuned for masses. Images found to be suspicious are given to a biorthogonal 4.4 classifier 72 tuned for masses, and images found then to be normal are placed in a normal bin 74. Images again found to be suspicious go to a Daubechies 2 classifier 76 tuned for masses, from which the images found to be normal are put in a normal bin 78 and the images found to be suspicious are put in a suspicious bin 80. Images classified as normal by the original Daubechies 8 classifier go to a biorthogonal 4.4 classifier 82 tuned for calcifications. Images found to be normal are placed in a normal bin 84 and images found to be suspicious are filtered by a Daubechies 2 classifier 86 tuned for calcifications into a normal bin 88 and a suspicious bin 90.

C. General Purpose and Commercial use Applications:

The main application is to sort images into higher and lower priority stacks for review by radiologists. The protocol does not make decisions on pathology, only that certain images contain suspicious features. These features need to be interpreted by an expert. The protocol can be implemented at any level, on-site in an x-ray office, in a specialized clinic or in a hospital. In addition, with the advent of PACS and jurisdiction wide availability of exams, the software can be deployed over the health network.

Our analysis of the challenges facing low density population areas indicates that the scarcity of radiologists represents a major obstacle to timely interpretation of mammography images. This protocol may assist health administrators in prioritizing the deployment of resources for mammographic interpretation. The commercial success of the protocol will be related to performance improvement achieved by the "triage" and cost savings realized.

Immaterial modifications may be made to the embodiments described here without departing from what is covered by the claims. In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

What is claimed is:

1. An image analyzer, comprising:
    a first stage configured to accept as input a digital image comprising pixel values and render the digital image comparable to properties of a training set of images;
    a second stage having as input the rendered digital image, the second stage being configured to apply to the rendered digital image at least one calculation to all pixel values in the rendered digital image to generate at least one single value representative of the digital image; and
    a classifier configured to operate on the at least one single value and comparable single values from the training set of images and produce a classification decision.

2. The image analyzer of claim 1 in which the second stage comprises a wavelet decomposition system for decomposing the digital image to plural levels of decomposition and a feature extractor for calculating a value of a property of the decomposed image.

3. The image analyzer of claim 2 in which the classifier is configured to determine a propensity for the image to fall into one of plural categories based on the value of the property of the wavelet decomposition of the image at the level of decomposition.

4. The image analyzer of claim 3 in which the classifier is configured to operate by aggregating the propensities determined for the image to fall into the one of plural categories for each of plural combinations of the choice of basis for wavelet decomposition, the level of decomposition, and the choice of property.

5. The image analyzer of claim 2 in which the wavelet decomposition system is configured to use one or more of a Haar wavelet, a Daubechies wavelet and a biorthogonal wavelet.

6. The image analyzer of claim 1 in which the first stage is configured to perform one or more of the following steps:
    A) orient the digital image;
    B) select an area of interest in the digital image and set all pixels not part of the area of interest to a brightness of zero;
    C) select an area of interest in the digital image and set all pixels not part of the area of interest to a brightness of zero using a brightness threshold;
    D) select an area of interest in the digital image comprising a single connected region of pixels and set all pixels not part of the area of interest to a brightness of zero using a brightness threshold;
    E) select an area of interest in the digital image comprising a single connected region of pixels that includes the center of the digital image, and set all pixels not part of the area of interest to a brightness of zero using a brightness threshold; and
    F) normalize the brightness of the digital image.

7. The image analyzer of claim 1 in which the second stage is configured to calculate at least one of:
    the mean brightness of the pixels;
    the standard deviation of the brightness of the pixels;
    the skewness of the brightness of the pixels; and
    the kurtosis of the brightness of the pixels.

8. The image analyzer of claim 1 in which one or more of the first stage, second stage and the classifier is configured to apply a correction based on one or more of size of features and directionality of the calculation.

9. Apparatus for determining a propensity for an image to fall into one of plural categories, comprising:
    a processing system for applying a wavelet decomposition to the image to plural levels of decomposition;
    a feature extractor for calculating a value for a property of the wavelet decomposition of the image at a level of decomposition;
    a classifier for determining a propensity for the image to fall into one of plural categories based on the value of the property of the wavelet decomposition of the image at the level of decomposition; and
    in which the classifier is configured to operate by aggregating the propensities determined for the image to fall into the one of plural categories for each of plural combinations of the choice of basis for wavelet decomposition, the level of decomposition, and the choice of property.

10. The apparatus of claim 9 in which the classifier is configured to determine the propensity for an image to fall into one of plural categories by dividing the possible values for the property into bins and for the bin into which the property falls, determining the probability based on the number of images from a training set of images which have values for the property within the bin and fall into the one of plural categories, and the number of images from a training set of images which have values for the property within the bin and do not fall into the one of plural categories.

11. The apparatus of claim 9 in which the processing system is configured to use one or more of a Haar wavelet, a Daubechies wavelet and a biorthogonal wavelet.

12. The apparatus of claim 9 in which the processing system is configured to at least one of:
    A) orient the digital image;
    B) select an area of interest in the digital image and set all pixels not part of the area of interest to a brightness of zero;
    C) select an area of interest in the digital image and set all pixels not part of the area of interest to a brightness of zero using a brightness threshold;
    D) select an area of interest in the digital image comprising a single connected region of pixels and set all pixels not part of the area of interest to a brightness of zero using a brightness threshold;
    E) select an area of interest in the digital image comprising a single connected region of pixels that includes the center of the digital image, and set all pixels not part of the area of interest to a brightness of zero using a brightness threshold; and
    F) normalize the brightness of the digital image.

13. The apparatus of claim 9 in which the feature extractor is configured to calculate at least one of:
    the mean brightness of the pixels;
    the standard deviation of the brightness of the pixels;
    the skew of the brightness of the pixels; and
    the kurtosis of the brightness of the pixels.

14. The apparatus of claim 9 in which one or more of the processing system, feature extractor and the classifier is configured to apply a correction based on one or more of size of features and directionality of the wavelet decomposition.

15. A method of reducing workload of a physician, comprising the steps of:
    obtaining a digital image of human tissue, the digital image comprising pixel values;

in at least a pre-classification step, processing the digital image to render the digital image comparable to properties of a training set of images;

applying at least one calculation to all pixel values in the digital image to generate at least one single value representative of the image;

classifying the digital image as normal or not-normal by comparing the at least one single value to comparable single values from the training set of images; and having the physician review the digital image only if the digital image is not-normal.

16. The method of claim 15 in which applying at least one calculation to all pixel values in the digital image comprises:

applying a wavelet decomposition to the image to plural levels of decomposition; and calculating a value for a property of the wavelet decomposition of the image at a level of decomposition.

17. The method of claim 16 in which classifying the digital image comprises determining a propensity for the image to fall into one of plural categories based on the value of the property of the wavelet decomposition of the image at the level of decomposition.

18. The method of claim 17 in which:

the steps of claim 18 are applied for plural combinations of the choice of basis for wavelet decomposition, the level of decomposition, and the choice of property; and a propensity for the image to fall into one of plural categories is determined by aggregating the propensities determined for the image to fall into the one of plural categories for each of the plural combinations.

19. The method of claim 17 in which the propensity for an image to fall into one of plural categories is a probability, and the step of determining the probability comprises the steps of:

dividing the possible values for the property into bins; and for the bin into which the property falls, determining the probability based on the number of images from a training set of images which have values for the property within the bin and fall into the one of plural categories, and the number of images from a training set of images which have values for the property within the bin and do not fall into the one of plural categories.

20. The method of claim 17 in which determining propensities is carried out (a) with a first combination of the choice of basis for wavelet decomposition, the level of decomposition, and the choice of property, to generate a propensity for the image to fall into one or more of the plural categories; and (b) with a second combination of the choice of basis for wavelet decomposition, the level of decomposition, and the choice of property, the second combination depending on the propensities determined with the first combination.

21. The method of claim 15 in which the image is a mammogram.

22. The method of claim 21 in which in at least a pre-classification step the image is oriented.

23. The method of claim 21 in which in at least a pre-classification step, an area of interest in the image is selected, and all pixels not part of the area of interest are set to a brightness of zero.

24. The method of claim 23 in which the area of interest is selected by means of a brightness threshold.

25. The method of claim 24 in which the brightness threshold is chosen based on Otsu's method.

26. The method of claim 24 in which the area of interest is selected as a single connected region of pixels meeting the threshold.

27. The method of claim 24 in which the single connected region containing the centre of the image is selected as the area of interest.

28. The method of claim 21 in which in at least a pre-classification, the brightness of the image is normalized.

29. The method of claim 17 in which only pixels which are nonzero in the approximation image for the level of decomposition at which the value is calculated are used in calculating the value for the property.

30. The method of claim 17 in which the property comprises the mean brightness of the pixels.

31. The method of claim 17 in which the property comprises the standard deviation of the brightness of the pixels.

32. The method of claim 17 in which the property comprises the skew of the brightness of the pixels.

33. The method of claim 17 in which the property comprises the kurtosis of the brightness of the pixels.

34. The method of claim 17 in which a Haar wavelet is used in the wavelet decomposition.

35. The method of claim 17 in which a Daubechies wavelet is used in the wavelet decomposition.

36. The method of claim 17 in which a biorthogonal wavelet is used in the wavelet decomposition.

37. A method of determining a propensity for an image to fall into one of plural categories, comprising the steps of:

1) applying a wavelet decomposition to the image to plural levels of decomposition;

2) calculating a value for a property of the wavelet decomposition of the image at a level of decomposition;

3) determining a propensity for the image to fall into one of plural categories based on the value of the property of the wavelet decomposition of the image at the level of decomposition: and in which the steps of 1), 2), and 3) are applied for plural combinations of the choice of basis for wavelet decomposition, the level of decomposition, and the choice of property; and a propensity for the image to fall into one of plural categories is determined by aggregating the propensities determined for the image to fall into the one of plural categories for each of the plural combinations.

38. The method of claim 37 in which the propensity for an image to fall into one of plural categories is a probability, and the step of determining the probability comprises the steps of:

dividing the possible values for the property into bins; and for the bin into which the property falls, determining the probability based on the number of images from a training set of images which have values for the property within the bin and fall into the one of plural categories, and the number of images from a training set of images which have values for the property within the bin and do not fall into the one of plural categories.

39. The method of claim 37 in which determining propensities is carried out (a) with a first set of combinations of the choice of basis for wavelet decomposition, the level of decomposition, and the choice of property, for the image to fall into one or more of the plural categories; and (b) with a second set of combinations of the choice of basis for wavelet decomposition, the level of decomposition, and the choice of property, the second set of combinations depending on the propensities determined with the first set of combinations.

40. The method of claim 39 in which in at least a pre-classification step the image is oriented.

41. The method of claim 39 in which in at least a pre-classification step, an area of interest in the image is selected, and all pixels not part of the area of interest are set to a brightness of zero.

42. The method of claim 41 in which the area of interest is selected by means of a brightness threshold.

43. The method of claim 42 in which the brightness threshold is chosen based on Otsu's method.

44. The method of claim 42 in which the area of interest is selected as a single connected region of pixels meeting the threshold.

45. The method of claim 42 in which the single connected region containing the centre of the image is selected as the area of interest.

46. The method of claim 39 in which in at least a pre-classification, the brightness of the image is normalized.

47. The method of claim 37 in which only pixels which are nonzero in the approximation image for the level of decomposition at which the value is calculated are used in calculating the value for the property.

48. The method of claim 37 in which the property comprises the mean brightness of the pixels.

49. The method of claim 37 in which the property comprises the standard deviation of the brightness of the pixels.

50. The method of claim 37 in which the property comprises the skew of the brightness of the pixels.

51. The method of claim 37 in which the property comprises the kurtosis of the brightness of the pixels.

52. The method of claim 37 in which a Haar wavelet is used in the wavelet decomposition.

\* \* \* \* \*